United States Patent [19]

Swanson

[11] Patent Number: 4,936,860
[45] Date of Patent: Jun. 26, 1990

[54] METAL SCAPHOID IMPLANT

[76] Inventor: Alfred B. Swanson, 2945 Bonnell, SE., Grand Rapids, Mich. 49506

[21] Appl. No.: 248,897

[22] Filed: Sep. 23, 1988

[51] Int. Cl.[5] ............................................. A61F 2/42
[52] U.S. Cl. .................................................... 623/21
[58] Field of Search ............................ 623/16, 18, 21

[56] References Cited

U.S. PATENT DOCUMENTS

| 3,745,590 | 7/1973 | Stubstad | 623/21 |
| 3,879,767 | 4/1975 | Stubstad | 623/21 |
| 3,924,276 | 12/1975 | Eaton | 623/21 |
| 4,164,793 | 8/1979 | Swanson | 623/21 |
| 4,198,712 | 4/1980 | Swanson | 623/21 |

OTHER PUBLICATIONS

Vitallium Surg. Appliance (catalog), Howmet Corp., New York, NY, 1964, pp. 54 and 84.
Article entitled "Reconstruction of the Thumb Basal Joints, Development and Current Status of Implant Techniques", by Alfred B. Swanson, M.D. and Genevieve De Groot Swanson, M.D.
Work entitled "Clinical Symposia, Reconstructive Surgery in the Arthritic Hand and Foot", vol. 31, No. 6 (1979) by Alfred B. Swanson.
Work entitled "Flexible Implant Resection Arthroplasty in the Hand and Extremeties", by Alfred B. Swanson, published 1973, pp. 1–6, 15, 16, 30, 31 and 240–253.

Primary Examiner—David J. Isabella
Attorney, Agent, or Firm—Price, Heneveld, Cooper, De Witt & Litton

[57] ABSTRACT

A scaphoid implant surgically insertable adjacent the trapezium, the trapezoid, the lunate, the capitate and the radius bones includes a rigid, metal body. The body defines a capitate articulating surface, a radius articulating surface and a lunate articulating surface. A stem extends from an inferior surface of the body. The stem defines a trapezium engaging ledge. The ledge when implanted engages the trapezium to prevent vertical or dorsal movement of the implant out of the plane of the wrist. The body defines a bore for receiving a suture to prevent rotation at the scapholunate junction.

7 Claims, 2 Drawing Sheets

METAL SCAPHOID IMPLANT

BACKGROUND OF THE INVENTION

The present invention relates to arthroplastic reconstruction of the human joints and more particularly to implant resection arthroplasty of the wrist joint.

Frequent causes of disability of the wrist joint include aseptic necrosis and arthritis of the carpal bones. Surgical treatment of wrist joint disabilities has heretofore included intercarpal fusion, wrist fusion, local resection, proximal row carpectamy, bone grafting, radial styloidectomy, radial shortening or ulnar lengthening and soft tissue interposition arthroplasty. Fusion procedures have an adverse effect on stability, power and mobility of the wrist. Local resection procedures involving the removal of irreversibly pathological bone are complicated by migration of adjacent carpal bones into the space left by the resection and resulting instability of the wrist joint.

Various forms of metallic, acrylic and silicone implants have been developed for replacement of carpal bones. The implants essentially act as articulating spacers to maintain the relationship of adjacent carpal bones after excision of the carpal bones they replace while preserving mobility of the wrist. Examples of prior carpal bone implants may be found in Applicant's work entitled "Flexible Implant Resection Arthroplasty On The Hand And Extremities", 1973 by C.V. Mosby Company; U.S. Pat. No. 4,198,712 entitled SCAPHOID IMPLANT and issued on Apr. 22, 1980 to the Applicant; and U.S. Pat. No. 4,164,793 entitled LUNATE IMPLANT and issued on Aug. 21, 1979 to Applicant.

The prior carpal scaphoid implants have been of two basic types. The implant described in Applicant's aforementioned work is shaped essentially as an anatomical replica of the carpal scaphoid. The implant does, however, have more pronounced concavities to provide for greater stability. The implant has an intramedullary stem that fits into the trapezium bone to maintain anatomical positioning postoperatively until a firm capsuloligamentous system has healed around the implant. The implant described in aforementioned U.S. Pat. No. 4,198,712 departs from the anatomical replication of the scaphoid bone. The implant includes an inferior surface defining a trapezium articulate facet and a trapezoid articulate facet. A stabilizing stem extends outwardly from the inferior surface. The implant further includes a superior surface having a smooth convex shape which articulates with the radius bone. An internal surface includes a flat, planar lunate articulate facet and a deep concavity adapted to articulate with the capitate bone. In one embodiment, the stabilizing stem is eliminated and the implant is fixed with a tendon segment or suture. The tendon segment or suture is inserted through a bore in the implant body to fix or inhibit dislocation of the implant.

SUMMARY OF THE INVENTION

In accordance with the present invention, a unique scaphoid implant is provided which eliminates problems heretofore experienced with bone shifting, loss of relationship between the implant and adjacent carpal bones and which overcomes a tendency of the implant to rotate or turn vertically. Essentially, the unique scaphoid implant includes a body defining several articulating surfaces. The body is more amorphous than the prior anatomical replica and defines a capitate articulating surface, a radius articulating surface and a lunate articulating surface. The body defines an extending trapezium engaging ledge. The ledge is adapted to be received within a "pocket" surgically formed in the palmar surface of the trapezium bone adjacent its proximal end. The contact or interference between the ledge and the trapezium bone prevents rotary movement of the implant.

DETAILED DESCRIPTION OF THE PREFERRED EMBODIMENT

Figure 1:
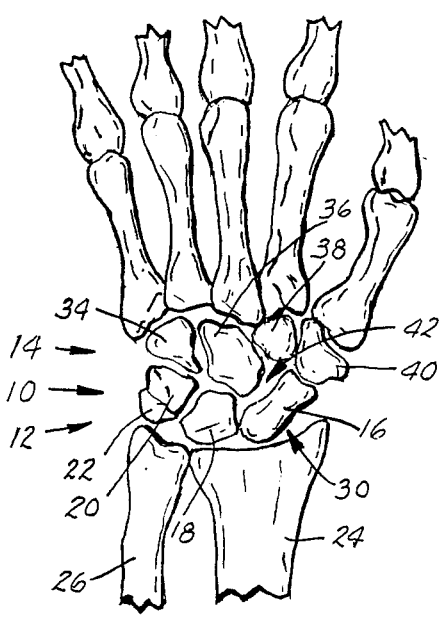
FIG. 1 is a fragmentary, posterior or dorsal view of the wrist joint of the left hand showing the distal and proximal carpal rows.

A posterior or dorsal view of the wrist joint of a left hand is illustrated in FIG. 1. Wrist joint 10 includes a proximal carpal row 12 and a distal carpal row 14. Proximal carpal row 12 includes a scaphoid bone 16, a lunate bone 18, a triquetrum bone 20 and a pisiform bone 22. The proximal row 12 is adjacent the radius 24 and the ulnar 26. A joint 30 extends along the proximal carpal row of the wrist between the distal radius. Joint 30 is referred to as the radiocarpal joint. Distal carpal row 14 includes the hamate bone 34, the capitate bone 36, the trapezoid bone 38 and the trapezium bone 40. The midcarpal joint 42 extends between the distal and proximal carpal rows. The scaphoid bone 16 articulates proximally about the radius 24, distally about the trapezium 40 and trapezoid 38 and medially about the lunate 18 and the capitate 36.

The carpal bones are held together by short, interosseous ligaments Ulnar collateral and radial collateral ligaments provide lateral support for the wrist. Palmar radiocarpal and dorsal radiocarpal ligaments maintain support of the carpal area. The fibers of the palmar radiocarpal ligament extend distally and obliquely from the radius, the triangular fibrocartilage and styloid process of the ulna. These ligaments define a symmetrical pattern due to insertions into the scaphoid, lunate, triquetrum and capitate bones.

Figure 2:
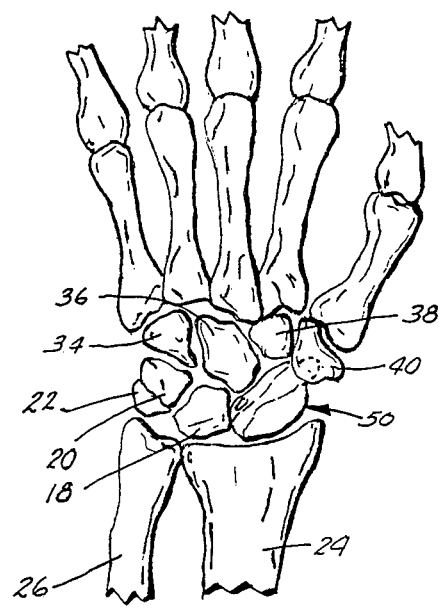
FIG. 2 is a fragmentary, posterior or dorsal view of the wrist joint of the left hand including a scaphoid implant in accordance with the present invention.
Figure 3:
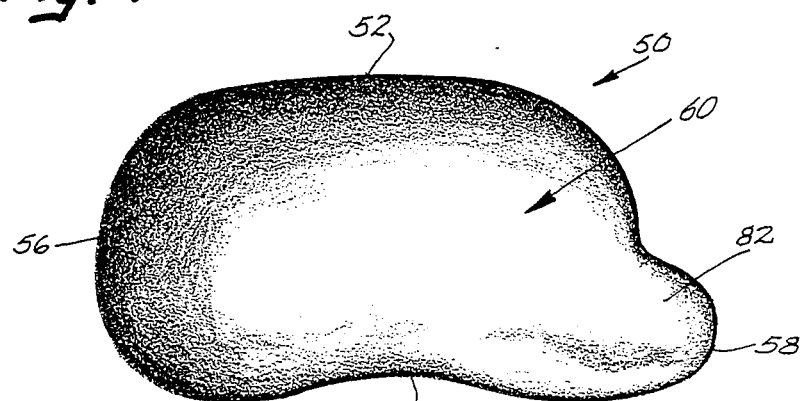
FIG. 3 is an elevational view of the external surface of the implant in accordance with the present invention.
Figure 4:
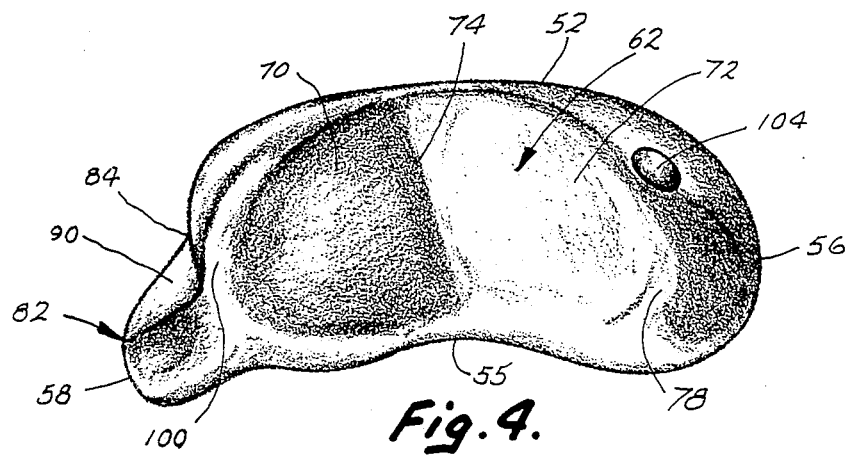
FIG. 4 is a perspective view showing the internal surface of the implant.
Figure 5:
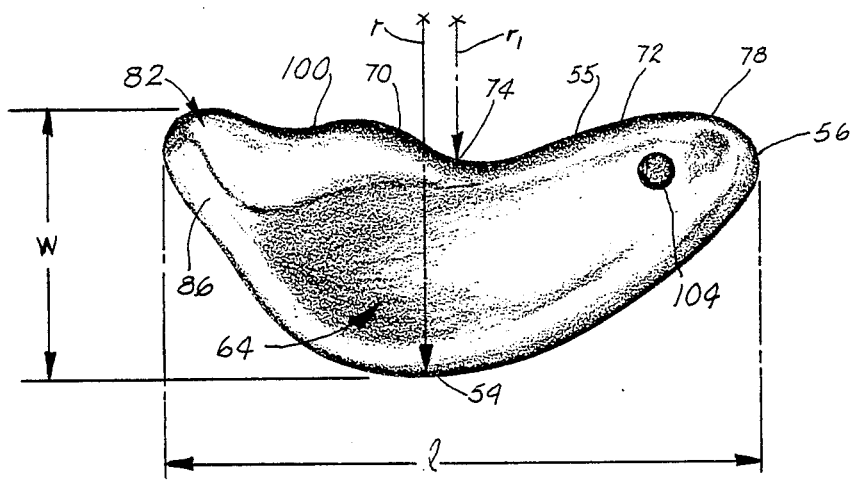
FIG. 5 is a plan view illustrating the palmar surface of the implant.
Figure 6:
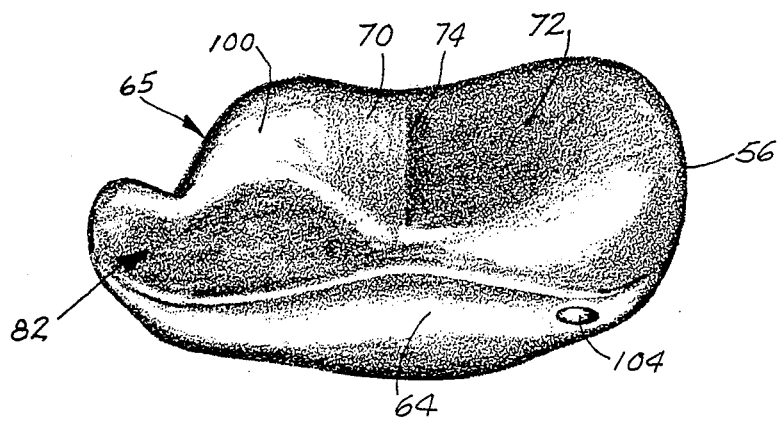
FIG. 6 is a perspective view illustrating the palmar and internal surfaces of the implant.

In accordance with the present invention, a scaphoid implant generally designated 50 is provided. As seen in FIG. 2, implant 50 articulates with the trapezium 40, the trapezoid 38, the capitate 36, the lunate 18 and the radius 24. As seen in FIGS. 3–8, implant 50 is a one-piece member or body. Implant 50, as seen in FIGS. 3, 4 and 5, defines a dorsal edge 52, a medial palmar edge 54, a lateral palmar edge 55, a proximal edge 56 and a distal edge 58. Edges 52, 54, 55, 56 and 58 are all smoothly curved. Implant 50 includes an external surface generally designated 60 (FIG. 3), an internal surface 62 (FIG. 4), a palmar or anterior surface 64 (FIG. 5), an inferior surface 65 (FIG. 7) and a superior surface 66 (FIG. 8). As seen in FIGS. 3, 5 and 8, external surface 60 is smoothly curved from proximal edge 56 to distal edge 58. Surface 60 defines a radius articulating surface which articulates with the distal end of the radius (FIG. 2). Implant 50, as seen in FIG. 8, has a generally triangular shape in end elevation. Palmar surface 64 defines the base of the triangle with the sides defined by external surface 60 and internal surface 62. These sides join to define dorsal edge 52.

Internal surface 62, as seen in FIGS. 4-7, defines a pair of slightly concave facets 70, 72. Facets 70, 72 join to define an apex 74. Surface 62 has a generally V-shaped configuration in horizontal cross section. Facet 72 is separated from proximal edge 56 by a curved, convex lunate articulating surface 78. Facets 70, 72 of surface 62 define a capitate articulating surface. This surface is similar in configuration to the capitate articulating surface of the anatomical scaphoid bone 16. As seen in FIG. 2, facets 70, 72 articulate with the capitate head 36. Surface 78 articulates with the lunate bone 18.

Figure 7:
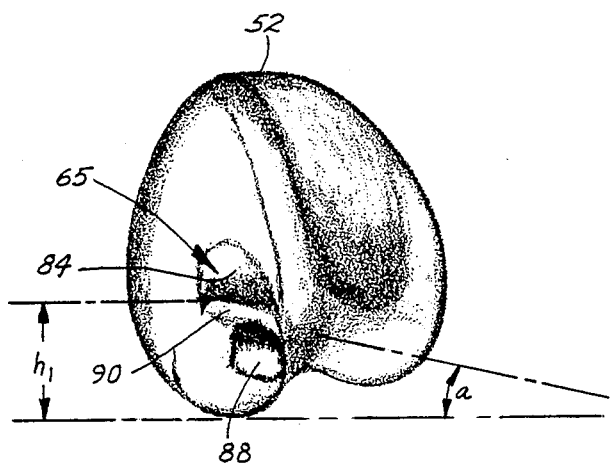
FIG. 7 is an end, elevational view illustrating the inferior surface and distal end of the implant.
Figure 8:
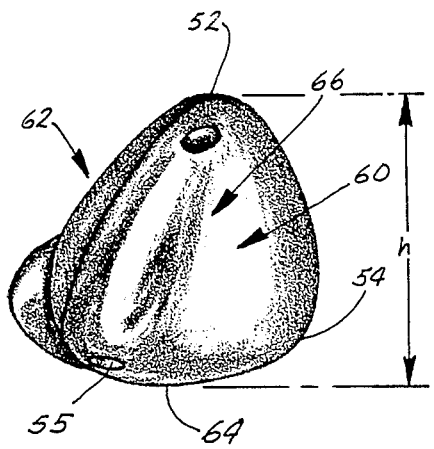
FIG. 8 is an end, elevational view illustrating the superior surface and proximal end of the implant.

As seen in FIGS. 4-7, a stem portion or protrusion 82 extends from an inferior surface facet 84 of the implant. Stem portion 82 includes a generally flat palmar surface portion 86, an inferior, rounded surface facet 88 and a dorsal ledge 90. The ledge in plan is generally triangular in shape including a base at surface facet 84 and a rounded apex at distal end 58. Ledge 90 is angled upwardly slightly from horizontal at an angle "a" (FIG. 7) and is generally perpendicular to inferior facet 84. Inferior surface 65, which includes stem 82 and facet 84, is generally triangular in shape in end elevation (FIG. 7). Surface 65 includes a base defined by palmar surface 64 and an apex along dorsal edge 52. Internal surface 62 between facet 70 and stem 82 defines a trapezoid articulating surface 100.

The implant, as seen in FIGS. 5 and 7, is generally semi-lunar in plan configuration. Palmar surface 64 has a semi-lunar shape from which surfaces 60, 62 extend. Implant 50, also as seen in FIGS. 4, 5, 6 and 8, defines a throughbore 104. Bore 104 extends from dorsal edge 52 through palmar surface 64 adjacent the proximal end 56 of the implant.

Implant 50 is not configured to replicate closely and in detail the scaphoid bone replaced. One form of prior implant was developed based upon a detailed and critical study of approximately 120 scaphoid bones. Such study resulted in a series of graduated implants which were anatomically similar to and mimic the bone replaced. Subsequently, it was determined that the significant number of anatomical surfaces created a tendency for the implant to lose its relationship with adjacent bones upon bone shifting. Such shifting occurs with wrist disease. Implant 50 does, however, loosely or generally mimic or approach the general configuration of the scaphoid bone. Implant 50 is more amorphous than the prior implants. Similarly, implant 50 does not define the facets and concavities of the implant illustrated in the aforementioned U.S. Pat. No. 4,198,712.

As seen in FIG. 2, implant 50 is positioned surgically adjacent trapezium 40, trapezoid 38, capitate 36, lunate 18 and radius 24. Implant 50 will articulate with the radius 24 along surface 60, the lunate 18 generally at surface 78, the capitate along the concavity or recess defined by surfaces 70, 72, with the trapezoid at articulating surface 100 and with the trapezium 40 at inferior facet 84 and ledge 90. The surgical procedure for implanting scaphoid 50 is substantially the same as that set forth in the aforementioned U.S. Pat. No. 4,198,712. With the present implant, however, the undersurface of trapezium 40 is resected to define a small pocket. Stem portion 82 extends under trapezium 40, and ledge 90 is disposed within the pocket. An intramedullary stem as employed in prior implants is not used to fix or stabilize the implant. As with the procedures described in detail in the aforementioned '712 patent, the scapho-lunate ligament may be reconstructed with a distally based slip of the extensor carpi radialis brevis tendon. The tendon slip may be passed through bore 104 and then securely fixed to itself with multiple sutures. In the alternative, a suture passed through bore 104 provides stabilization to the palmar ligaments at the scapholunate junction. The suture prevents rotation at the junction.

In order to insure a proper fit, the implant in accordance with the present invention is fabricated in proportionally increased sizes. Essentially, the same basic overall sizes or types as used with prior implants may be employed. Also, due to the mirror image differences between the right and left wrist, right and left mirror image implants must be provided. Larger sized implants basically result from proportional size increases.

In a presently existing embodiment of the scaphoid implant 50, the overall longitudinal dimension "l" (FIG. 5) of the body from proximal edge 56 to distal edge 58 of surface 60 is approximately 1.05 inches. The overall width "w" (FIG. 5) of the body at the palmar surface between the medial palmar edge 54 and the lateral palmar edge 55 is approximately 0.416 inch. Surface 60 defines a radius "r" at edge 54 of approximately 0.62 inch. Edge 55 adjacent apex 74 defines a radius "$r_1$" of approximately 0.375 inch. Ledge 90 has a length of approximately 0.17 inch and a width of approximately 0.20 inch. The angle "a" (FIG. 7) is approximately 12 to 15 degrees. The implant has a maximum height "h" (FIG. 8) of approximately 0.510 inch. The maximum height "$h_1$" (FIG. 7) of stem portion 82 is approximately 0.26 inch. It is presently preferred that the implant be fabricated as a rigid, one-piece member from a medical grade metal material such as Vitallium.

The implant in accordance with the present invention is relatively easily manufactured employing conventional molding techniques. The implant is surgically positioned through relatively simple surgical procedures. The implant has the potential for permitting wrist motion with increased stability, mobility and freedom from pain from that heretofore obtained. The unique trapezium ledge prevents a naturally occurring rotary motion, luxation or dislocation of the implant caused by the intercarpal ligamentous structures.

In view of the foregoing description, those of ordinary skill in the art may envision modifications which would not depart from the inventive concepts disclosed herein. Therefore, the above description should be considered as that of the preferred embodiment. The true spirit and scope of the present invention may be determined by reference to the appended claims.

The embodiments of the invention in which an exclusive property or privilege is claimed are defined as follows:

1. A scaphoid implant surgically insertable adjacent the trapezium, the trapezoid, the lunate, the capitate and the radius, said implant adapted to cooperate with a pocket formed surgically in a palmar surface of the trapezium, said implant comprising:

an elongated body, said body defining:
- an inferior surface having a generally triangular shape in plan and including an apex and a base;
- an external surface extending from said inferior surface and having a generally concave shape in plan;
- an internal surface extending from said inferior surface, said external and internal surfaces joining to define a dorsal edge and a proximal edge, said dorsal edge being smoothly curved and extending generally from said inferior surface apex to said proximal edge; and
- a stem extending distally from said inferior surface at said base, said stem adapted to extend under the trapezium and said stem defining a trapezium ledge, said ledge dimensioned to engage a surgically formed pocket in the palmar surface of the trapezium to prevent rotary movement of the implant.

2. A scaphoid implant as defined by claim 1 wherein said internal surface defines a concave capitate recess and a curved lunate surface.

3. A scaphoid implant as defined by claim 2 wherein said capitate recess has a generally curved, V shape in horizontal cross section.

4. A scaphoid implant as defined by claim 1 wherein said body further defines:
- a palmar surface which is generally semi-lunar shaped in plan and is bonded by a palmar edge of said internal surface, a palmar edge of said external surface, said proximal edge and said stem.

5. A scaphoid implant as defined by claim 2 wherein said body further defines:
- a palmar surface which is generally semi-lunar shaped in plan and is bonded by a palmar edge of said internal surface, a palmar edge of said external surface, said proximal edge and said stem.

6. A scaphoid implant as defined by claim 3 wherein said body further defines:
- a palmar surface which is generally semi-lunar shaped in plan and is bonded by a palmar edge of said internal surface, a palmar edge of said external surface, said proximal edge and said stem.

7. A scaphoid implant as defined by claim 1 wherein said body defines a bore therethrough.

* * * * *